(12) United States Patent
Sun et al.

(10) Patent No.: US 12,097,204 B2
(45) Date of Patent: Sep. 24, 2024

(54) SOLID PHARMACEUTICAL COMPOSITION CONTAINING 1,3,5-TRIAZINE DERIVATIVE OR SALT THEREOF

(71) Applicants: CHIA TAI TIANQING PHARMACEUTICAL GROUP CO., LTD., Jiangsu (CN); LIANYUNGANG RUNZHONG PHARMACEUTICAL CO., LTD., Lianyungang (CN); CENTAURUS BIOPHARMA CO., LTD., Beijing (CN)

(72) Inventors: Yuanyuan Sun, Lianyungang (CN); Shan Zhou, Lianyungang (CN); Lei Liu, Lianyungang (CN); Ping Dong, Lianyungang (CN); Jing Gao, Lianyungang (CN); Laicun Li, Lianyungang (CN); Zhilin Chen, Lianyungang (CN); Yi Xu, Lianyungang (CN); Shang Wang, Lianyungang (CN)

(73) Assignees: CHIA TAI TIANQING PHARMACEUTICAL GROUP CO., LTD., Lianyungang (CN); LIANYUNGANG RUNZHONG PHARMACEUTICAL CO., LTD., Lianyungang (CN); CENTAURUS BIOPHARMA CO., LTD., Beijing (CN)

( * ) Notice: Subject to any disclaimer, the term of this patent is extended or adjusted under 35 U.S.C. 154(b) by 788 days.

(21) Appl. No.: 17/272,915

(22) PCT Filed: Sep. 3, 2019

(86) PCT No.: PCT/CN2019/104191
§ 371 (c)(1),
(2) Date: Mar. 2, 2021

(87) PCT Pub. No.: WO2020/048449
PCT Pub. Date: Mar. 12, 2020

(65) Prior Publication Data
US 2021/0275534 A1    Sep. 9, 2021

(30) Foreign Application Priority Data

Sep. 3, 2018    (CN) .......................... 201811021176.X (51) Int. Cl.
*A61K 31/53*    (2006.01)
*A61K 9/20*    (2006.01)
*A61K 47/14*    (2017.01)

(52) U.S. Cl.
CPC .............. *A61K 31/53* (2013.01); *A61K 47/14* (2013.01); *A61K 9/2095* (2013.01)

(58) Field of Classification Search
CPC ....... A61K 31/53; A61K 47/14; A61K 9/2095
See application file for complete search history.

(56) References Cited

U.S. PATENT DOCUMENTS

2007/0259049 A1    11/2007    Kotar-Jordan et al.
2015/0297521 A1    10/2015    To et al.

FOREIGN PATENT DOCUMENTS

CN    101137371 A    3/2008
CN    104968332 A    10/2015
(Continued)

OTHER PUBLICATIONS

CN Office Action in Application No. 201980052490.0 dated Feb. 7, 2022.
(Continued)

*Primary Examiner* — Kamal A Saeed
(74) *Attorney, Agent, or Firm* — Maschoff Brennan (57) ABSTRACT

A solid pharmaceutical composition containing a 1,3,5-triazine derivative or a pharmaceutically acceptable salt thereof and a preparation method therefor. In particular, involved are a solid pharmaceutical composition containing 4-(tert-butoxyamino)-6-(6-(trifluoromethyl)pyridin-2-yl)-N-(2-(trifluoromethyl)pyridin-4-yl)-1,3,5-triazine-2-amine or a pharmaceutically acceptable salt thereof and a preparation method therefor. The solid pharmaceutical composition has a good stability, a fast dissolution rate and a high bioavailability, and is suitable for clinical production and use.

17 Claims, 2 Drawing Sheets

(56) References Cited

FOREIGN PATENT DOCUMENTS

| CN | 106265547 A | 1/2017 |
| CN | 106539768 A | 3/2017 |
| CN | 107641114 A | 1/2018 |
| WO | 2017/016513 A1 | 2/2017 |
| WO | 2018/133856 A1 | 7/2018 |

OTHER PUBLICATIONS

Bhakay et al., "Recovery of BCS Class II drugs during aqueous redispersion of core-shell type nanocomposite particles produced via fluidized bed coating" Power Technology 236 (2013 221-234, Jan. 5, 2012.

Gao et al., "Pharmacological characterization of TQ05310, a potent inhibitor of isocitrate deyhydrogenase 2 R140Q and R172K mutants" Cancer Science Weekly, Jul. 26, 2019.

SOLID PHARMACEUTICAL COMPOSITION CONTAINING 1,3,5-TRIAZINE DERIVATIVE OR SALT THEREOF

CROSS-REFERENCE TO RELATED APPLICATIONS

The present application claims priority and benefit to the Chinese Patent Application No. 201811021176.X, filed with National Intellectual Property Administration, PRC on Sep. 3, 2018, the disclosure of which is incorporated herein by reference in its entirety.

TECHNICAL FIELD

The present application relates to the technical field of pharmaceuticals, specifically to a solid pharmaceutical composition comprising a 1,3,5-triazine derivative or a pharmaceutically acceptable salt thereof and a preparation method thereof, and more specifically to a solid pharmaceutical composition comprising 4-(tert-butoxyamino)-6-(6-(trifluoromethyl)pyridin-2-yl)-N-(2-(trifluoromethyl)pyridin-4-yl)-1,3,5-triazin-2-amine or a pharmaceutically acceptable salt thereof, a preparation method thereof and use thereof.

BACKGROUND

IDH is known as isocitrate dehydrogenase, and is the most important key enzyme in the tricarboxylic acid cycle in cells. It catalyzes the oxidative decarboxylation of isocitrate, producing 2-oxoglutarate (i.e., alpha-ketoglutarate). IDH mutations are found in various tumors (such as glioma, sarcoma, acute myelocytic leukemia and the like), and are located at arginine residues of the catalytic site (IDH1/R132H, IDH2/R140Q, IDH2/R172K). About 15% of acute myeloid leukemia (AML) patients carry IDH2 mutations, with the rate increasing with age.

International Patent Application No. WO2017/016513 discloses in Example 3 a compound 4-(tert-butoxyamino)-6-(6-(trifluoromethyl)pyridin-2-yl)-N-(2-(trifluoromethyl)pyridin-4-yl)-1,3,5-triazin-2-amine having the structure of formula I, and a preparation method thereof:

Formula I

The compound of formula I is an IDH2 inhibitor and can be used for treating cancer induced by IDH2 mutation, wherein the IDH2 mutation may be IDH2/R140Q and/or IDH2/R172K mutation. Oral administration is the most common route of administration for drugs. By oral administration, the drug may be absorbed at a number of sites along the gastrointestinal tract including the stomach, duodenum, jejunum, ileum, and colon. Different chemical environments of the gastrointestinal tract will influence the dissolving and release of the pharmaceutical agent, thereby influencing the absorption of the active substance in the pharmaceutical agent. The pH is 1-3.5 in stomach and 4-8 in small intestine, and may significantly influence pH-dependent solubility and permeability.

The compound of formula I and the pharmaceutically acceptable salt disclosed herein feature poor solubility in either acidic or basic condition, and is hardly soluble in water. Due to the physicochemical properties of the compound of formula I and the pharmaceutically acceptable salt thereof, the drug features poor hydrophilic and infiltrating characteristics, and is unfavorable for dissolving and absorption of the drug in the gastrointestinal tract after oral administration, resulting in low bioavailability and compromised efficacy. Therefore, there is a need for developing pharmaceutical preparations to satisfy the requirements of efficacy and safety, solubility and bioavailability, and controlled release in clinical use.

In order to solve the above problems, the present application provides a solid pharmaceutical composition comprising a compound of formula I or a pharmaceutically acceptable salt thereof. The solid pharmaceutical composition has good stability, high dissolution rate and bioavailability, and is suitable for manufacturing and clinical use.

SUMMARY

The present invention provides a solid pharmaceutical composition comprising a compound of formula I or a pharmaceutically acceptable salt thereof, wherein the composition comprises the compound of formula I or the pharmaceutically acceptable salt thereof as an active ingredient and at least one pharmaceutically acceptable excipient.

In some embodiments, the above solid pharmaceutical compositions may be used for treating a cancer induced by an IDH2 mutation, including: glioblastoma (neuroglioma), myelodysplastic syndrome (MDS), myeloproliferative neoplasm (MPN), acute myeloid leukemia (AML), sarcoma, melanoma, non-small cell lung cancer, chondrosarcoma, bile duct cancer or angioimmunoblastic non-Hodgkin's lymphoma (NHL). The subject is a mammal, preferably a human.

The pharmaceutically acceptable salt disclosed herein is selected from hydrochloride, hydrobromide, sulfate, phosphate, methanesulfonate, ethanesulfonate, p-toluenesulfonate, maleate, oxalate, citrate, malonate, acetate, benzoate, glutarate, D-tartrate, L-tartrate and fumarate; preferably hydrochloride, sulfate, methanesulfonate, p-toluenesulfonate and maleate; more preferably hydrochloride, methanesulfonate and p-toluenesulfonate.

For the pharmaceutically acceptable salt of the compound of formula I disclosed herein, the molar ratio of the compound of formula I to the acid radical forming the pharmaceutically acceptable salt can be selected from 2:1, 1:1, 1:2, and 1:3, depending on whether the compound of formula I and the acid radical form a stable salt.

The solid pharmaceutical composition disclosed herein comprises 10-100 mg, preferably 30-80 mg, and more preferably 50-60 mg of the compound of formula I or the pharmaceutically acceptable salt thereof.

In the solid pharmaceutical composition, the compound of formula I or the pharmaceutically acceptable salt thereof is present in an amount of 0.5-50 wt %, preferably 0.5-30 wt %, and more preferably 1-25 wt %, based on the total mass of the solid pharmaceutical composition.

In some embodiments, the excipient of the solid pharmaceutical composition comprising the compound of formula I or the pharmaceutically acceptable salt thereof includes a diluent, a binder, a disintegrant and a lubricant.

In some embodiments, the diluent is selected from: starch, pregelatinized starch, sucrose, lactose, fructose, maltose, trehalose, pullulan, polydextrose, dextrin, maltodextrin, microcrystalline cellulose, cellulose acetate, ethylcellulose, mannitol, sorbitol, erythritol, isomaltitol, lactitol, maltitol, polyethylene glycol, xylitol, sorbitol, calcium carbonate, calcium phosphate, calcium sulfate, magnesium carbonate, magnesium oxide, sodium carbonate, sodium bicarbonate, sodium chloride, and a mixture of any two or more thereof; preferably, microcrystalline cellulose, lactose, starch, mannitol, xylitol, and a mixture of microcrystalline cellulose with other diluents; and more preferably, microcrystalline cellulose, lactose, starch, mannitol, xylitol, a mixture of microcrystalline cellulose and lactose, a mixture of microcrystalline cellulose and starch, a mixture of microcrystalline cellulose and mannitol, and a mixture of microcrystalline cellulose and xylitol. The diluent is present in an amount of 10-90 wt %, preferably 20-85 wt %, 25-80 wt %, 25-75 wt %, 30-75 wt %, 40-75 wt %, 45-75 wt %, 50-75 wt %, 55-75 wt %, or 60-75 wt %, based on the solid pharmaceutical composition. When the diluent is selected from a mixture of microcrystalline cellulose and other diluents, the microcrystalline cellulose is present in an amount of 10-90 wt %, preferably 20-85 wt %, 25-80 wt %, 25-75 wt %, 30-75 wt %, 40-75 wt %, 45-75 wt %, 50-75 wt %, 55-75 wt %, or 60-75 wt %, based on the diluent.

In some embodiments, the binder is selected from: povidone, starch slurry, dextrin, powder sugar, syrup, cellulose derivatives (e.g., hydroxypropyl methylcellulose, methylcellulose, carboxymethyl cellulose, ethyl cellulose, hydroxyethyl cellulose, hydroxypropyl cellulose), sodium alginate, polyethylene glycol, magnesium aluminum silicate, N-vinylpyrrolidone, gum arabic, and a mixture of any two or more thereof; preferably, povidone, hydroxypropyl methylcellulose, hydroxypropyl cellulose, carboxymethyl cellulose, starch slurry and dextrin; and more preferably hydroxypropyl methylcellulose, hydroxypropyl cellulose and povidone. The binder is present in an amount of 1-10 wt %, preferably 2 wt %, 2.5 wt %, 3 wt %, 3.5 wt %, 4 wt %, 4.5 wt %, 5 wt %, 5.5 wt %, 6 wt %, 6.5 wt %, 7 wt %, 7.5 wt %, 8 wt %, 8.5 wt %, 9 wt % or 9.5 wt %, based on the solid pharmaceutical composition.

In some embodiments, the disintegrant is selected from: dry starch, sodium starch glycolate, sodium carboxymethyl starch, low-substituted hydroxypropyl cellulose, methylcellulose, croscarmellose sodium, sodium carboxymethyl cellulose, calcium carboxymethyl cellulose, crospovidone, alginic acid, calcium alginate, sodium alginate, chitosan, colloidal silicon dioxide, glycine, guar gum, magnesium aluminum silicate and povidone; preferably dry starch, sodium starch glycolate, sodium carboxymethyl starch, low-substituted hydroxypropyl cellulose, methylcellulose, crospovidone, croscarmellose sodium, sodium carboxymethyl cellulose and calcium carboxymethyl cellulose; and more preferably croscarmellose sodium, sodium carboxymethyl starch, crospovidone and low substituted hydroxypropyl cellulose. The disintegrant is present in an amount of 1-10 wt %, preferably 2 wt %, 2.5 wt %, 3 wt %, 3.5 wt %, 4 wt %, 4.5 wt %, 5 wt %, 5.5 wt %, 6 wt %, 6.5 wt %, 7 wt %, 7.5 wt %, 8 wt %, 8.5 wt %, 9 wt % or 9.5 wt %, based on the solid pharmaceutical composition. In some embodiments, the lubricant is selected from: stearic acid, calcium stearate, sodium stearate, zinc stearate, magnesium stearate, glyceryl monostearate, glyceryl behenate, glyceryl dibehenate, glyceryl tribehenate, palmitoyl stearyl glyceride, leucine, myristic acid, palmitic acid, poloxamer, polyethylene glycol, potassium benzoate, sodium benzoate, sodium lauryl sulfate, magnesium lauryl sulfate, sodium stearyl fumarate and talc powder; preferably, stearic acid, calcium stearate, sodium stearate, zinc stearate, magnesium stearate, glyceryl behenate, sodium lauryl sulfate, magnesium lauryl sulfate, glyceryl monostearate and sodium stearyl fumarate; and more preferably, magnesium stearate, glyceryl behenate, sodium lauryl sulfate and sodium stearyl fumarate. The lubricant is present in an amount of 0.5-5 wt %, preferably 0.8 wt %, 1.0 wt %, 1.2 wt %, 1.5 wt %, 1.8 wt %, 2.0 wt %, 2.2 wt %, 2.5 wt %, 2.8 wt %, 3.0 wt %, 3.2 wt %, 3.5 wt %, 3.8 wt %, 4.0 wt %, 4.2 wt %, 4.5 wt % or 4.8 wt %, based on the solid pharmaceutical composition.

In the solid pharmaceutical composition, the compound of formula I or the pharmaceutically acceptable salt thereof is selected from: the compound of formula I, monohydrochloride of the compound of formula I, dihydrochloride of the compound of formula I, trihydrochloride of the compound of formula I, monomethanesulfonate of the compound of formula I, dimethanesulfonate of the compound of formula I, trimethanesulfonate of the compound of formula I, mono-p-toluenesulfonate of the compound of formula I, di-p-toluenesulfonate of the compound of formula I, and tri-p-toluenesulfonate of the compound of formula I; preferably the compound of formula I, monomethanesulfonate of the compound of formula I, dimethanesulfonate of the compound of formula I and trimethanesulfonate of the compound of formula I; and more preferably monomethanesulfonate of the compound of formula I.

In some embodiments, the solid pharmaceutical composition may further comprise a solubilizer selected from: hydroxypropyl methylcellulose, polyoxyethylene alkyl ethers, polyoxyethylene castor oil derivatives, polyoxyethylene sorbitan fatty acid esters, polyethylene glycol 15 hydroxystearate, sodium dodecyl sulfate, magnesium dodecyl sulfate, sorbitan esters, glyceryl caprylate, glyceryl trioleate, polyoxylglycerides, povidone, pyrrolidone, poloxamer, phospholipids and vitamin E polyethylene glycol succinate; and preferably sodium dodecyl sulfate and magnesium dodecyl sulfate. The solubilizer is present in an amount of 0.5-5 wt %, preferably 0.8 wt %, 1.0 wt %, 1.2 wt %, 1.5 wt %, 2.0 wt %, 2.2 wt %, 2.5 wt %, 2.8 wt %, 3.0 wt %, 3.2 wt %, 3.5 wt %, 3.8 wt %, 4.0 wt %, 4.2 wt %, 4.5 wt % or 4.8 wt %, based on the solid pharmaceutical composition.

The solid pharmaceutical compositions disclosed herein may be in a variety of dosage forms suitable for oral administration to human, including, for example, tablets, pills, capsules, powders, granules and the like. In some embodiments, the present invention provides a tablet comprising a tablet core comprising the solid pharmaceutical composition described above. The tablet may be coated or uncoated.

The coating may be selected from a film coating. The film-forming material of the film coating is selected according to the functions required by the preparation, such as gastric dissolving, enteric dissolving, sustained release, special stability and the like. The film-forming material may be selected from conventional film coating materials, such as hydroxypropyl methylcellulose, hydroxypropyl ethylcellulose, hydroxypropyl cellulose, methylcellulose, hydroxyethyl cellulose, hydroxypropyl methylcellulose acetate succinate, hydroxypropyl methylcellulose phthalate, film-forming acrylic polymers, methacrylic acid-methyl methacrylate copolymers, film-forming vinyl polymers, polyvinyl alcohol and polyvinyl acetate phthalate; may be selected from sustained release coating materials, such as methacrylate copolymer, ethyl cellulose and cellulose acetate; or may be selected from enteric coating materials such as cellulose acetate phthalate, polyvinyl alcohol phthalate, methacrylate copolymer, cellulose acetate trimellitate, hydroxypropyl cellulose phthalate and hydroxypropyl cellulose succinate. The amount of the film-forming material is selected according to the function required by the film coating. Optionally, the film-forming material is present in an amount of 30% to 90%, for example, 30%, 40%, 50%, 60%, 70%, 80% or 90%, based on the film coating by weight. Optionally, the film-forming material is present in an amount of 0.5% to 5%, for example, 0.5%, 1.0%, 1.5%, 2.0%, 2.5%, 3.0%, 3.5%, 4.0%, 4.5% or 5.0%, based on the solid pharmaceutical composition disclosed herein by weight.

Optionally, the film coating comprises additional components, such as plasticizers, colorants, dispersion aids, or opacifiers. The plasticizers improve the film flexibility and durability as well as the adhesion property of the film coating. Suitable plasticizers include, for example, glycerol, acetylated monoglycerides, citrates (e.g., triethyl citrate), propylene glycol, polyethylene glycols (e.g., polyethylene glycol), triacetin (e.g., glyceryl triacetate), triglycerides (e.g., castor oil), or phthalates (e.g., diethyl phthalate). Typically, the plasticizers, when used, is present in an amount of 1% to 20%, for example, 5% to 15%, based on the film coating by weight. Suitable opacifiers and colorants are well known and include, for example, titanium dioxide, iron sesquioxide (e.g., iron(III) oxide). Suitable dispersion aids include, for example, talc.

In some embodiments, suitable film coatings may be from commercially available concentrates that can be diluted with water prior to adding to the composition. The concentrate may include cellulose ethers and plasticizers, e.g., the Opaspray™ coating materials from Colorcon.

In another aspect of the present application, the solid pharmaceutical composition comprising the compound of formula I or the pharmaceutically acceptable salt thereof is a solid dispersion. The carrier material of the solid dispersion composition is selected from cellulose derivatives, polyethylene glycol, poloxamer, polyvinylpyrrolidone, copovidone and crospovidone.

In some embodiments, the cellulose-based compound as a carrier material is enteric, and is selected from cellulose acetate phthalate (CAP), hydroxypropyl methylcellulose phthalate (HPMCP), hydroxypropyl methylcellulose acetate succinate (HPMCAS), and carboxymethyl ethyl cellulose (CMEC); preferably, the cellulose-based compound is selected from hydroxypropyl methylcellulose phthalate (HPMCP) and hydroxypropyl methylcellulose acetate succinate (HPMCAS).

In some embodiments, the carrier material is present in an amount of 40-90%, optionally 40%, 45%, 50%, 55%, 60%, 65%, 70%, 75%, 80%, 85% or 90% by weight, preferably 60-80% by weight, and more preferably 70% by weight, based on the solid dispersion by weight.

In some embodiments, the solid dispersion may further comprise a stabilizer, including vitamin E, dibutylhydroxytoluene, butylhydroxyanisole, soy lecithin, ascorbic acid, citric acid, and cysteine hydrochloride; and preferably, vitamin E, ascorbic acid and butylhydroxyanisole. Suitably, the stabilizer is present in an amount of 0.05-0.50%, optionally 0.05%, 0.10%, 0.15%, 0.20%, 0.25%, 0.30%, 0.35%, 0.40%, 0.45%, or 0.50% by weight, preferably 0.10-0.30% by weight, and more preferably 0.20% by weight, based on the solid dispersion by weight.

In some embodiments, the solid dispersion comprises 10-40 wt % of the compound of formula I or the pharmaceutically acceptable salt thereof, 60-80 wt % of a carrier material, and 0.10-0.30 wt % of a stabilizer. In some embodiments, the compound of formula I or the pharmaceutically acceptable salt thereof is selected from: the compound of formula I, monohydrochloride of the compound of formula I, dihydrochloride of the compound of formula I, trihydrochloride of the compound of formula I, monomethanesulfonate of the compound of formula I, dimethanesulfonate of the compound of formula I, trimethanesulfonate of the compound of formula I, mono-p-toluenesulfonate of the compound of formula I, di-p-toluenesulfonate of the compound of formula I, and tri-p-toluenesulfonate of the compound of formula I; the carrier material is selected from hydroxypropyl methylcellulose phthalate (HPMCP) and hydroxypropyl methylcellulose acetate succinate (HPMCAS); and the stabilizer is selected from butylhydroxyanisole.

In some embodiments, the solid dispersion comprises 10-40 wt % of the compound of formula I or the pharmaceutically acceptable salt thereof, 60-80 wt % of a carrier material, and 0.10-0.30 wt % of a stabilizer. In some embodiments, the compound of formula I or the pharmaceutically acceptable salt thereof is selected from: the compound of formula I, monomethanesulfonate of the compound of formula I, dimethanesulfonate of the compound of formula I, and trimethanesulfonate of the compound of formula I; the carrier material is selected from hydroxypropyl methylcellulose phthalate (HPMCP) and hydroxypropyl methylcellulose acetate succinate (HPMCAS); and the stabilizer is selected from butylhydroxyanisole.

The solid dispersion disclosed herein can be prepared into a general pharmaceutical preparation in the form of, for example, but not limited to, powders, tablets, pills, capsules, or the like, by known methods using excipients as needed such as diluents, disintegrants, binders, lubricants, colorants, suspending agents, sweeteners, surfactants, and the like.

Examples of diluent include starch, pregelatinized starch, sucrose, lactose, fructose, maltose, trehalose, pullulan, polydextrose, dextrin, maltodextrin, microcrystalline cellulose, cellulose acetate, ethylcellulose, mannitol, sorbitol, erythritol, isomaltitol, lactitol, maltitol, polyethylene glycol, xylitol, sorbitol, calcium carbonate, calcium phosphate, calcium sulfate, magnesium carbonate, magnesium oxide, sodium carbonate, sodium bicarbonate, sodium chloride, and a mixture of any two or more thereof.

Examples of disintegrant include dry starch, sodium starch glycolate, sodium carboxymethyl starch, low-substituted hydroxypropyl cellulose, methylcellulose, croscarmellose sodium, sodium carboxymethyl cellulose, calcium carboxymethyl cellulose, crospovidone, alginic acid, calcium alginate, sodium alginate, chitosan, colloidal silicon dioxide, glycine, guar gum, magnesium aluminum silicate and povidone.

Examples of binder include hydroxypropyl cellulose, hydroxypropyl methylcellulose, polyvinylpyrrolidone, pregelatinized starch, syrup, or starch syrup.

Examples of lubricant include stearic acid, calcium stearate, sodium stearate, zinc stearate, magnesium stearate, glyceryl monostearate, glyceryl behenate, glyceryl dibehenate, glyceryl tribehenate, palmitoyl stearyl glyceride, leucine, myristic acid, palmitic acid, poloxamer, polyethylene glycol, potassium benzoate, sodium benzoate, sodium lauryl sulfate, magnesium lauryl sulfate, sodium stearyl fumarate or talc powder.

Examples of colorant include yellow iron oxide, brown iron oxide, red iron oxide, titanium oxide, brilliant blue FCF, rose bengal, or lemon yellow.

Examples of suspending agent include polysorbate, polyethylene glycol, gum arabic, glycerol or gelatin.

Examples of sweetener include aspartame, saccharin, sodium saccharin, starch syrup or fructose.

Examples of the surfactant include sodium dodecyl sulfate, polysorbate, or polyoxyethylene hydrogenated castor oil.

Capsules can be prepared according to known methods by mixing a solid dispersion of the aforementioned compound of formula I or the pharmaceutically acceptable salt thereof with any of the aforementioned excipients, and filling the mixture into hard capsules made of gelatin, hydroxypropyl methylcellulose, polyvinyl alcohol, or the like, or into soft capsules based on gelatin. In some embodiments of the present invention, the solid pharmaceutical composition of the present invention comprising the compound of formula I or the pharmaceutically acceptable salt thereof may comprise: a mixture comprising the compound of formula I or the pharmaceutically acceptable salt thereof, and a fluidization excipient. In some embodiments, the solid pharmaceutical composition further comprises an additional excipient. In some embodiments, the solid pharmaceutical composition comprising the compound of formula I or the pharmaceutically acceptable salt thereof is prepared by fluidized bed granulation.

In some embodiments, the compound of formula I or the pharmaceutically acceptable salt thereof is selected from: the compound of formula I, monohydrochloride of the compound of formula I, dihydrochloride of the compound of formula I, trihydrochloride of the compound of formula I, monomethanesulfonate of the compound of formula I, dimethanesulfonate of the compound of formula I, trimethanesulfonate of the compound of formula I, mono-p-toluenesulfonate of the compound of formula I, di-p-toluenesulfonate of the compound of formula I, and tri-p-toluenesulfonate of the compound of formula I; preferably the compound of formula I, monomethanesulfonate of the compound of formula I, dimethanesulfonate of the compound of formula I and trimethanesulfonate of the compound of formula I; and more preferably monomethanesulfonate of the compound of formula I.

In some embodiments, the compound of formula I or the pharmaceutically acceptable salt thereof is present in an amount of 0.5-50 wt %, preferably 0.5-30 wt %, and more preferably 1-25 wt %, based on the total mass of the solid pharmaceutical composition.

In some embodiments, the mixture comprising the compound of formula I or the pharmaceutically acceptable salt thereof further comprises a binder, a diluent, and a solubilizer. In some embodiments, the binder is selected from: hydroxypropyl methylcellulose, hydroxypropyl cellulose, and povidone; and preferably, hydroxypropyl methylcellulose and hydroxypropyl cellulose. In some embodiments, the diluent is selected from: microcrystalline cellulose, lactose, starch, mannitol, xylitol, a mixture of microcrystalline cellulose and lactose, a mixture of microcrystalline cellulose and starch, a mixture of microcrystalline cellulose and mannitol, and a mixture of microcrystalline cellulose and xylitol; and preferably, lactose and mannitol. In some embodiments, the solubilizer is selected from sodium dodecyl sulfate and magnesium dodecyl sulfate; and preferably, sodium dodecyl sulfate.

In some embodiments, the mixture comprising the compound of formula I or the pharmaceutically acceptable salt thereof further comprises a binder and a diluent. In some embodiments, the binder is selected from: hydroxypropyl methylcellulose, hydroxypropyl cellulose, and povidone; and preferably, hydroxypropyl methylcellulose and hydroxypropyl cellulose. In some embodiments, the diluent is selected from: microcrystalline cellulose, lactose, starch, mannitol, xylitol, a mixture of microcrystalline cellulose and lactose, a mixture of microcrystalline cellulose and starch, a mixture of microcrystalline cellulose and mannitol, and a mixture of microcrystalline cellulose and xylitol; and preferably, lactose and mannitol.

In some embodiments, the mixture comprising the compound of formula I or the pharmaceutically acceptable salt thereof further comprises a binder and a solubilizer. In some embodiments, the binder is selected from: hydroxypropyl methylcellulose, hydroxypropyl cellulose, and povidone; and preferably, hydroxypropyl methylcellulose and hydroxypropyl cellulose. In some embodiments, the solubilizer is selected from sodium dodecyl sulfate and magnesium dodecyl sulfate; and preferably, sodium dodecyl sulfate.

In some embodiments, the mixture comprising the compound of formula I or the pharmaceutically acceptable salt thereof further comprises a binder. In some embodiments, the binder is selected from: hydroxypropyl methylcellulose, hydroxypropyl cellulose, and povidone; and preferably, hydroxypropyl methylcellulose and hydroxypropyl cellulose.

In some embodiments, the fluidization excipient comprises a diluent and a disintegrant. In some embodiments, the diluent is selected from: microcrystalline cellulose, lactose, starch, mannitol, xylitol, a mixture of microcrystalline cellulose and lactose, a mixture of microcrystalline cellulose and starch, a mixture of microcrystalline cellulose and mannitol, and a mixture of microcrystalline cellulose and xylitol; and preferably, microcrystalline cellulose, a mixture of microcrystalline cellulose and lactose, and a mixture of microcrystalline cellulose and mannitol. In some embodiments, the disintegrant is selected from: croscarmellose sodium, sodium carboxymethyl starch, crospovidone, and low substituted hydroxypropyl cellulose; and preferably, croscarmellose sodium.

In some embodiments, the additional excipient comprises a lubricant selected from: magnesium stearate, glyceryl behenate, sodium lauryl sulfate, and sodium stearyl fumarate; and preferably, magnesium stearate.

The diluent in the mixture comprising the compound of formula I or the pharmaceutically acceptable salt thereof is present in an amount of 10-50 wt %, preferably 15-50 wt %, and more preferably 17-35 wt %, based on the total amount of the diluents in the solid pharmaceutical composition.

In some embodiments, the mixture comprising the compound of formula I or the pharmaceutically acceptable salt thereof further comprises a binder and a diluent. In some embodiments, the binder is selected from: hydroxypropyl methylcellulose, hydroxypropyl cellulose, and povidone; and preferably, hydroxypropyl methylcellulose and hydroxypropyl cellulose. In some embodiments, the diluent is selected from: microcrystalline cellulose, lactose, starch, mannitol, xylitol, a mixture of microcrystalline cellulose and lactose, a mixture of microcrystalline cellulose and starch, a mixture of microcrystalline cellulose and mannitol, and a mixture of microcrystalline cellulose and xylitol; and preferably, lactose and mannitol.

In some embodiments, the mixture comprising the compound of formula I or the pharmaceutically acceptable salt thereof further comprises hydroxypropyl methylcellulose and mannitol. In some embodiments, hydroxypropyl methylcellulose in the mixture is generally present in an amount of 1-10 wt %, preferably 1-5 wt %, and more preferably 2-5 wt %, based on the total mass of the solid pharmaceutical composition. In some embodiments, mannitol in the mixture is generally present in an amount of 1-45 wt %, preferably 5-30 wt %, more preferably 5-20 wt %, based on the total mass of the solid pharmaceutical composition. In a specific embodiment, the mass ratio of the compound of formula I or the pharmaceutically acceptable salt thereof to mannitol in the mixture is generally 1:0.5 to 1:10, preferably 1:0.5 to 1:5, and more preferably 1:0.5 to 1:2.

In some embodiments, the mixture comprising the compound of formula I or the pharmaceutically acceptable salt thereof further comprises a binder and a solubilizer. In some embodiments, the binder is selected from: hydroxypropyl methylcellulose, hydroxypropyl cellulose, and povidone; and preferably, hydroxypropyl methylcellulose and hydroxypropyl cellulose. In some embodiments, the solubilizer is selected from sodium dodecyl sulfate and magnesium dodecyl sulfate; and preferably, sodium dodecyl sulfate.

In some embodiments, the mixture comprising the compound of formula I or the pharmaceutically acceptable salt thereof further comprises hydroxypropyl methylcellulose and sodium dodecyl sulfate. In some embodiments, hydroxypropyl methylcellulose in the mixture is generally present in an amount of 1-10 wt %, preferably 1-5 wt %, and more preferably 2-5 wt %, based on the total mass of the solid pharmaceutical composition. In some embodiments, sodium dodecyl sulfate in the mixture is generally present in an amount of 0.5-5 wt %, preferably 0.5-2 wt %, and more preferably 0.5-1 wt %, based on the total mass of the solid pharmaceutical composition.

In some embodiments, the mixture comprising the compound of formula I or the pharmaceutically acceptable salt thereof further comprises a binder, a diluent, and a solubilizer. In some embodiments, the binder is selected from: hydroxypropyl methylcellulose, hydroxypropyl cellulose, and povidone; and preferably, hydroxypropyl methylcellulose and hydroxypropyl cellulose. In some embodiments, the diluent is selected from: microcrystalline cellulose, lactose, starch, mannitol, xylitol, a mixture of microcrystalline cellulose and lactose, a mixture of microcrystalline cellulose and starch, a mixture of microcrystalline cellulose and mannitol, and a mixture of microcrystalline cellulose and xylitol; and preferably, lactose and mannitol. In some embodiments, the solubilizer is selected from sodium dodecyl sulfate and magnesium dodecyl sulfate; and preferably, sodium dodecyl sulfate.

In some embodiments, the mixture comprising the compound of formula I or the pharmaceutically acceptable salt thereof further comprises hydroxypropyl methylcellulose, mannitol and sodium dodecyl sulfate. In some embodiments, hydroxypropyl methylcellulose in the mixture is generally present in an amount of 1-10 wt %, preferably 1-5 wt %, and more preferably 2-5 wt %, based on the total mass of the solid pharmaceutical composition. In some embodiments, mannitol in the mixture is generally present in an amount of 1-45 wt %, preferably 5-30 wt %, and more preferably 5-20 wt %, based on the total mass of the solid pharmaceutical composition. In a specific embodiment, the mass ratio of the compound of formula I or the pharmaceutically acceptable salt thereof to mannitol in the mixture is generally 1:1 to 1:10, preferably 1:1 to 1:5, and more preferably 1:1 to 1:2. In some embodiments, sodium dodecyl sulfate in the mixture is generally present in an amount of 0.5-5 wt %, preferably 0.5-2 wt %, and more preferably 0.5-1 wt %, based on the total mass of the solid pharmaceutical composition.

In some embodiments, the mixture comprising the compound of formula I or the pharmaceutically acceptable salt thereof further comprises hydroxypropyl cellulose, mannitol and sodium dodecyl sulfate. In some embodiments, hydroxypropyl cellulose in the mixture is generally present in an amount of 1-10 wt %, preferably 1-5 wt %, and more preferably 2-5 wt %, based on the total mass of the solid pharmaceutical composition. In some embodiments, mannitol in the mixture is generally present in an amount of 1-45 wt %, preferably 5-30 wt %, and more preferably 5-20 wt %, based on the total mass of the solid pharmaceutical composition. In a specific embodiment, the mass ratio of the compound of formula I or the pharmaceutically acceptable salt thereof to mannitol in the mixture is generally 1:1 to 1:10, preferably 1:1 to 1:5, and more preferably 1:1 to 1:2. In some embodiments, sodium dodecyl sulfate in the suspension is generally present in an amount of 0.5-5 wt %, preferably 0.5-2 wt %, and more preferably 0.5-1 wt %, based on the total mass of the solid pharmaceutical composition.

In some embodiments, the mixture comprising the compound of formula I or the pharmaceutically acceptable salt thereof further comprises hydroxypropyl methylcellulose, lactose and sodium dodecyl sulfate. In some embodiments, hydroxypropyl methylcellulose in the mixture is generally present in an amount of 1-10 wt %, preferably 1-5 wt %, and more preferably 2-5 wt %, based on the total mass of the solid pharmaceutical composition. In some embodiments, lactose in the mixture is generally present in an amount of 1-45 wt %, preferably 5-30 wt %, more preferably 5-20 wt %, based on the total mass of the solid pharmaceutical composition. In a specific embodiment, the mass ratio of the compound of formula I or the pharmaceutically acceptable salt thereof to lactose in the mixture is generally 1:1 to 1:10, preferably 1:1 to 1:5, and more preferably 1:1 to 1:2. In some embodiments, sodium dodecyl sulfate in the mixture is generally present in an amount of 0.5-5 wt %, preferably 0.5-2 wt %, and more preferably 0.5-1 wt %, based on the total mass of the solid pharmaceutical composition.

In some embodiments, the fluidization excipient comprises a diluent and a disintegrant. The diluent is selected from: microcrystalline cellulose, lactose, starch, mannitol, xylitol, a mixture of microcrystalline cellulose and lactose, a mixture of microcrystalline cellulose and starch, a mixture of microcrystalline cellulose and mannitol, and a mixture of microcrystalline cellulose and xylitol; and preferably, microcrystalline cellulose, a mixture of microcrystalline cellulose and lactose, and a mixture of microcrystalline cellulose and mannitol. In some embodiments, the disintegrant is selected from: croscarmellose sodium, sodium carboxymethyl starch, crospovidone, and low substituted hydroxypropyl cellulose; and preferably, croscarmellose sodium.

In some embodiments, when the diluent in the fluidization excipient is a mixture of microcrystalline cellulose and another diluent, the another diluent may or may not be of the same kind as that of the diluent in the mixture comprising the compound of formula I or the pharmaceutically acceptable salt thereof; preferably, the diluents are of the same kind.

In some embodiments, the fluidization excipient comprises microcrystalline cellulose and croscarmellose sodium.

In some embodiments, the fluidization excipient comprises microcrystalline cellulose, mannitol and croscarmellose sodium. In a specific embodiment, the mass ratio of microcrystalline cellulose to mannitol in the fluidization excipient is 1:1 to 9:1, preferably 1:1 to 5:1, and more preferably 2:1 to 4:1.

In some embodiments, the additional excipient comprises a lubricant. The lubricant is selected from: magnesium stearate, glyceryl behenate, sodium lauryl sulfate, and sodium stearyl fumarate; and preferably, magnesium stearate.

In another aspect, the present application provides a method for preparing a solid pharmaceutical composition comprising the compound of formula I or the pharmaceutically acceptable salt thereof, the method being fluidized bed granulation. Specifically, the method comprises the following steps: (1) preparing a suspension comprising the active ingredient; (2) preparing a fluidization excipient; (3) placing the fluidization excipient in step (2) into a fluidized bed reactor, and spraying the suspension comprising the active ingredient into the fluidized bed for granulation; and (4) sizing.

In a preferred embodiment, the method further comprises a step (5), mixing an additional excipient with the sized material.

In some embodiments, in step (1), the solvent of the suspension is selected from: methanol, ethanol, isopropanol, acetone, water, and any combination thereof; preferably, water and a mixture of ethanol and water; and more preferably, water.

In some embodiments, in step (1), the active ingredient in the suspension is selected from: the compound of formula I, monohydrochloride of the compound of formula I, dihydrochloride of the compound of formula I, trihydrochloride of the compound of formula I, monomethanesulfonate of the compound of formula I, dimethanesulfonate of the compound of formula I, trimethanesulfonate of the compound of formula I, mono-p-toluenesulfonate of the compound of formula I, di-p-toluenesulfonate of the compound of formula I, and tri-p-toluenesulfonate of the compound of formula I; preferably the compound of formula I, monomethanesulfonate of the compound of formula I, dimethanesulfonate of the compound of formula I and trimethanesulfonate of the compound of formula I; and more preferably monomethanesulfonate of the compound of formula I.

In some embodiments, in step (1), the mass ratio of active ingredient to solvent in the suspension is 1:5 to 1:20, preferably 1:5 to 1:15, and more preferably 1:5 to 1:10.

In some embodiments, in addition to the active ingredient, the suspension of step (1) comprises a binder, a diluent, and a solubilizer. In some embodiments, the binder is selected from: hydroxypropyl methylcellulose, hydroxypropyl cellulose, and povidone; and preferably, hydroxypropyl methylcellulose and hydroxypropyl cellulose. In some embodiments, the diluent is selected from: microcrystalline cellulose, lactose, starch, mannitol, xylitol, a mixture of microcrystalline cellulose and lactose, a mixture of microcrystalline cellulose and starch, a mixture of microcrystalline cellulose and mannitol, and a mixture of microcrystalline cellulose and xylitol; and preferably, lactose and mannitol. In some embodiments, the solubilizer is selected from sodium dodecyl sulfate and magnesium dodecyl sulfate; and preferably, sodium dodecyl sulfate.

In some preferred embodiments, in step (1), the compound of formula I or the pharmaceutically acceptable salt thereof is first mixed with the binder, the diluent and/or the solubilizer to give a mixture comprising the compound of formula I or the pharmaceutically acceptable salt thereof, and then the mixture is mixed with the solvent to give the suspension comprising the compound of formula I or the pharmaceutically acceptable salt thereof.

In some embodiments, in addition to the active ingredient, the suspension of step (1) comprises a binder and a diluent. In some embodiments, the binder is selected from: hydroxypropyl methylcellulose, hydroxypropyl cellulose, and povidone; and preferably, hydroxypropyl methylcellulose and hydroxypropyl cellulose. In some embodiments, the diluent is selected from: microcrystalline cellulose, lactose, starch, mannitol, xylitol, a mixture of microcrystalline cellulose and lactose, a mixture of microcrystalline cellulose and starch, a mixture of microcrystalline cellulose and mannitol, and a mixture of microcrystalline cellulose and xylitol; and preferably, lactose and mannitol.

In some embodiments, in addition to the active ingredient, the suspension of step (1) comprises a binder and a solubilizer. In some embodiments, the binder is selected from: hydroxypropyl methylcellulose, hydroxypropyl cellulose, and povidone; and preferably, hydroxypropyl methylcellulose and hydroxypropyl cellulose. In some embodiments, the solubilizer is selected from sodium dodecyl sulfate and magnesium dodecyl sulfate; and preferably, sodium dodecyl sulfate.

In some embodiments, in addition to the active ingredient, the suspension of step (1) comprises a binder. In some embodiments, the binder is selected from: hydroxypropyl methylcellulose, hydroxypropyl cellulose, and povidone; and preferably, hydroxypropyl methylcellulose and hydroxypropyl cellulose.

In some embodiments, in step (2), the fluidization excipient comprises a diluent and a disintegrant.

In some embodiments, the diluent is selected from: microcrystalline cellulose, lactose, starch, mannitol, xylitol, a mixture of microcrystalline cellulose and lactose, a mixture of microcrystalline cellulose and starch, a mixture of microcrystalline cellulose and mannitol, and a mixture of microcrystalline cellulose and xylitol; and preferably, microcrystalline cellulose, a mixture of microcrystalline cellulose and lactose, and a mixture of microcrystalline cellulose and mannitol. In some embodiments, the disintegrant is selected from: croscarmellose sodium, sodium carboxymethyl starch, crospovidone, and low substituted hydroxypropyl cellulose; and preferably, croscarmellose sodium.

In some embodiments, in step (5), the additional excipient comprises a lubricant selected from: magnesium stearate, glyceryl behenate, sodium lauryl sulfate, and sodium stearyl fumarate; and preferably, magnesium stearate.

In some embodiments, the method for preparing the solid pharmaceutical composition comprising the compound of formula I or the pharmaceutically acceptable salt thereof comprises: (1) preparing a suspension comprising the active ingredient, a binder, a diluent and a solubilizer; (2) mixing a diluent of a remaining amount with a disintegrant to give a fluidization excipient; (3) placing the fluidization excipient of step (2) into a fluidized bed reactor, and spraying the suspension of step (1) into the fluidized bed for granulation; and (4) sizing. In some preferred embodiments, the preparation method further comprises a step (5), mixing a lubricant with the sized material. In some embodiments, the binder is selected from: hydroxypropyl methylcellulose, hydroxypropyl cellulose, and povidone; and preferably, hydroxypropyl methylcellulose and hydroxypropyl cellulose. In some embodiments, the diluent in step (1) is selected from: microcrystalline cellulose, lactose, starch, mannitol, xylitol, a mixture of microcrystalline cellulose and lactose, a mixture of microcrystalline cellulose and starch, a mixture of microcrystalline cellulose and mannitol, and a mixture of microcrystalline cellulose and xylitol; and preferably, lactose and mannitol. In some embodiments, the solubilizer is selected from sodium dodecyl sulfate and magnesium dodecyl sulfate; and preferably, sodium dodecyl sulfate. In some embodiments, the disintegrant is selected from: croscarmellose sodium, sodium carboxymethyl starch, crospovidone, and low substituted hydroxypropyl cellulose; and preferably, croscarmellose sodium. In some embodiments, the lubricant is selected from: magnesium stearate, glyceryl behenate, sodium lauryl sulfate, and sodium stearyl fumarate; and preferably, magnesium stearate. In some embodiments, the diluent of the remaining amount in step (2) is selected from: microcrystalline cellulose, lactose, starch, mannitol, xylitol, a mixture of microcrystalline cellulose and lactose, a mixture of microcrystalline cellulose and starch, a mixture of microcrystalline cellulose and mannitol, and a mixture of microcrystalline cellulose and xylitol; and preferably, microcrystalline cellulose, a mixture of microcrystalline cellulose and lactose, and a mixture of microcrystalline cellulose and mannitol. The diluent in the step (1) is present in an amount of 10-50 wt %, preferably 15-50 wt %, and more preferably 17-35 wt %, based on the total amount of the diluents in the solid pharmaceutical composition.

In some embodiments, the method for preparing the solid pharmaceutical composition comprising the compound of formula I or the pharmaceutically acceptable salt thereof comprises: (1) preparing a suspension comprising the active ingredient, a binder and a diluent; (2) mixing a diluent of a remaining amount with a disintegrant to give a fluidization excipient; (3) placing the fluidization excipient of step (2) into a fluidized bed reactor, and spraying the suspension of step (1) into the fluidized bed for granulation; and (4) sizing. In some preferred embodiments, the preparation method further comprises a step (5), mixing a lubricant with the sized material. In some embodiments, in step (1), the binder is selected from: hydroxypropyl methylcellulose, hydroxypropyl cellulose, and povidone; and preferably, hydroxypropyl methylcellulose and hydroxypropyl cellulose. In some preferred embodiments, in step (1), the diluent is selected from microcrystalline cellulose, lactose, starch, mannitol, xylitol, a mixture of microcrystalline cellulose and lactose, a mixture of microcrystalline cellulose and starch, a mixture of microcrystalline cellulose and mannitol, and a mixture of microcrystalline cellulose and xylitol, and preferably lactose and mannitol; the disintegrant is selected from croscarmellose sodium, sodium carboxymethyl starch, crospovidone and low substituted hydroxypropyl cellulose, and preferably croscarmellose sodium; and the lubricant is selected from: magnesium stearate, glyceryl behenate, sodium lauryl sulfate and sodium stearyl fumarate, and preferably magnesium stearate. In some preferred embodiments, in step (2), the diluent of the remaining amount is selected from: microcrystalline cellulose, lactose, starch, mannitol, xylitol, a mixture of microcrystalline cellulose and lactose, a mixture of microcrystalline cellulose and starch, a mixture of microcrystalline cellulose and mannitol, and a mixture of microcrystalline cellulose and xylitol; and preferably, microcrystalline cellulose, a mixture of microcrystalline cellulose and lactose, and a mixture of microcrystalline cellulose and mannitol. The diluent in the step (1) is present in an amount of 10-50 wt %, preferably 15-50 wt %, and more preferably 17-35 wt %, based on the total amount of the diluents in the solid pharmaceutical composition.

In some embodiments, the method for preparing the solid pharmaceutical composition comprising the compound of formula I or the pharmaceutically acceptable salt thereof comprises: (1) preparing a suspension comprising the active ingredient, a binder and a solubilizer; (2) mixing a diluent with a disintegrant to give a fluidization excipient; (3) placing the fluidization excipient of step (2) into a fluidized bed reactor, and spraying the suspension of step (1) into the fluidized bed for granulation; and (4) sizing. In some embodiments, the preparation method comprises a step (5), mixing a lubricant with the sized material. In some embodiments, the binder is selected from: hydroxypropyl methylcellulose, hydroxypropyl cellulose, and povidone; and preferably, hydroxypropyl methylcellulose and hydroxypropyl cellulose. In some embodiments, the solubilizer is selected from sodium dodecyl sulfate and magnesium dodecyl sulfate; and preferably, sodium dodecyl sulfate. In some embodiments, the diluent is selected from: microcrystalline cellulose, lactose, starch, mannitol, xylitol, a mixture of microcrystalline cellulose and lactose, a mixture of microcrystalline cellulose and starch, a mixture of microcrystalline cellulose and mannitol, and a mixture of microcrystalline cellulose and xylitol; and preferably, microcrystalline cellulose, a mixture of microcrystalline cellulose and lactose, and a mixture of microcrystalline cellulose and mannitol. In some embodiments, the disintegrant is selected from: croscarmellose sodium, sodium carboxymethyl starch, crospovidone, and low substituted hydroxypropyl cellulose; and preferably, croscarmellose sodium. In some embodiments, the lubricant is selected from: magnesium stearate, glyceryl behenate, sodium lauryl sulfate, and sodium stearyl fumarate; and preferably, magnesium stearate.

In some embodiments, in the method for preparing a solid pharmaceutical composition comprising the compound of formula I or the pharmaceutically acceptable salt thereof, the air input in the fluidized bed reactor is 200-1000 m$^3$/h, preferably 500-800 m$^3$/h.

In some embodiments, in the method for preparing a solid pharmaceutical composition comprising the compound of formula I or the pharmaceutically acceptable salt thereof, the air input temperature in the fluidized bed reactor is 40-80° C., preferably 60-75° C.

In some embodiments, in the method for preparing a solid pharmaceutical composition comprising the compound of formula I or the pharmaceutically acceptable salt thereof, the suspension is sprayed into the fluidized bed at an atomization pressure of 1-5 bar, preferably 1.5-3 bar.

In the method for preparing a solid pharmaceutical composition comprising the compound of formula I or the pharmaceutically acceptable salt thereof, the fluidized bed granulation process further comprises drying to remove the solvent from the suspension, as needed after step (3). The temperature for drying is 40-75° C., and preferably 60-75° C.

In one embodiment, the present application provides a solid pharmaceutical composition comprises monomethanesulfonate of the compound of formula I, wherein the solid pharmaceutical composition is prepared by fluidizing the following components: a suspension comprising the monomethanesulfonate of the compound of formula I, and a fluidization excipient. In some embodiments, the components further comprise an additional excipient.

In some embodiments, the solvent in the suspension comprising the monomethanesulfonate of the compound of formula I is selected from methanol, ethanol, isopropanol, acetone, water, and any combination thereof; preferably water, and a mixture of ethanol and water; and more preferably water.

In some embodiments, the mass ratio of the monomethanesulfonate of the compound of formula I to the solvent in the suspension is 1:5 to 1:20, preferably 1:5 to 1:15, and more preferably 1:5 to 1:10.

In some embodiments, the monomethanesulfonate of the compound of formula I is present in an amount of 0.5-50 wt %, preferably 0.5-30 wt %, and more preferably 1-25 wt %, based on the total mass of the solid pharmaceutical composition.

In some embodiments, the suspension comprising the monomethanesulfonate of the compound of formula I further comprises a binder and a diluent. In some embodiments, the binder is selected from: hydroxypropyl methylcellulose, hydroxypropyl cellulose, and povidone; and preferably, hydroxypropyl methylcellulose and hydroxypropyl cellulose. In some embodiments, the diluent is selected from: microcrystalline cellulose, lactose, starch, mannitol, xylitol, a mixture of microcrystalline cellulose and lactose, a mixture of microcrystalline cellulose and starch, a mixture of microcrystalline cellulose and mannitol, and a mixture of microcrystalline cellulose and xylitol; and preferably, lactose and mannitol.

In some embodiments, the suspension comprising the monomethanesulfonate of the compound of formula I further comprises hydroxypropyl methylcellulose and mannitol. In some embodiments, hydroxypropyl methylcellulose in the suspension is generally present in an amount of 1-10 wt %, preferably 1-5 wt %, and more preferably 2-5 wt %, based on the total mass of the solid pharmaceutical composition. In some embodiments, mannitol in the suspension is generally present in an amount of 1-45 wt %, preferably 5-30 wt %, more preferably 5-20 wt %, based on the total mass of the solid pharmaceutical composition. In a specific embodiment, the mass ratio of the monomethanesulfonate of the compound of formula I to mannitol in the suspension is generally 1:0.5 to 1:10, preferably 1:0.5 to 1:5, and more preferably 1:0.5 to 1:2.

In some embodiments, the suspension comprising the monomethanesulfonate of the compound of formula I further comprises a binder and a solubilizer. In some embodiments, the binder is selected from: hydroxypropyl methylcellulose, hydroxypropyl cellulose, and povidone; and preferably, hydroxypropyl methylcellulose and hydroxypropyl cellulose. In some embodiments, the solubilizer is selected from sodium dodecyl sulfate and magnesium dodecyl sulfate; and preferably, sodium dodecyl sulfate.

In some embodiments, the suspension comprising the monomethanesulfonate of the compound of formula I further comprises hydroxypropyl methylcellulose and sodium dodecyl sulfate. In some embodiments, hydroxypropyl methylcellulose in the suspension is generally present in an amount of 1-10 wt %, preferably 1-5 wt %, and more preferably 2-5 wt %, based on the total mass of the solid pharmaceutical composition. In some embodiments, sodium dodecyl sulfate in the suspension is generally present in an amount of 0.5-5 wt %, preferably 0.5-2 wt %, and more preferably 0.5-1 wt %, based on the total mass of the solid pharmaceutical composition.

In some embodiments, the suspension comprising the monomethanesulfonate of the compound of formula I further comprises a binder, a diluent, and a solubilizer. In some embodiments, the binder is selected from: hydroxypropyl methylcellulose, hydroxypropyl cellulose, and povidone; and preferably, hydroxypropyl methylcellulose and hydroxypropyl cellulose. In some embodiments, the diluent is selected from: microcrystalline cellulose, lactose, starch, mannitol, xylitol, a mixture of microcrystalline cellulose and lactose, a mixture of microcrystalline cellulose and starch, a mixture of microcrystalline cellulose and mannitol, and a mixture of microcrystalline cellulose and xylitol; and preferably, lactose and mannitol. In some embodiments, the solubilizer is selected from sodium dodecyl sulfate and magnesium dodecyl sulfate; and preferably, sodium dodecyl sulfate.

In some embodiments, the suspension comprising the monomethanesulfonate of the compound of formula I further comprises hydroxypropyl methylcellulose, mannitol and sodium dodecyl sulfate.

In some embodiments, hydroxypropyl methylcellulose in the suspension is generally present in an amount of 1-10 wt %, preferably 1-5 wt %, and more preferably 2-5 wt %, based on the total mass of the solid pharmaceutical composition. In some embodiments, mannitol in the suspension is generally present in an amount of 1-45 wt %, preferably 5-30 wt %, and more preferably 5-20 wt %, based on the total mass of the solid pharmaceutical composition. In a specific embodiment, the mass ratio of the monomethanesulfonate of the compound of formula I to mannitol in the suspension is generally 1:1 to 1:10, preferably 1:1 to 1:5, and more preferably 1:1 to 1:2. In some embodiments, sodium dodecyl sulfate in the suspension is generally present in an amount of 0.5-5 wt %, preferably 0.5-2 wt %, and more preferably 0.5-1 wt %, based on the total mass of the solid pharmaceutical composition.

In some embodiments, the suspension comprising the monomethanesulfonate of the compound of formula I further comprises hydroxypropyl cellulose, mannitol, and sodium dodecyl sulfate. In some embodiments, hydroxypropyl cellulose in the suspension is generally present in an amount of 1-10 wt %, preferably 1-5 wt %, and more preferably 2-5 wt %, based on the total mass of the solid pharmaceutical composition. In some embodiments, mannitol in the suspension is generally present in an amount of 1-45 wt %, preferably 5-30 wt %, and more preferably 5-20 wt %, based on the total mass of the solid pharmaceutical composition. In a specific embodiment, the mass ratio of the monomethanesulfonate of the compound of formula I to mannitol in the suspension is generally 1:1 to 1:10, preferably 1:1 to 1:5, and more preferably 1:1 to 1:2. In some embodiments, sodium dodecyl sulfate in the suspension is generally present in an amount of 0.5-5 wt %, preferably 0.5-2 wt %, and more preferably 0.5-1 wt %, based on the total mass of the solid pharmaceutical composition.

In some embodiments, the suspension comprising the monomethanesulfonate of the compound of formula I further comprises hydroxypropyl methylcellulose, lactose and sodium dodecyl sulfate. In some embodiments, hydroxypropyl methylcellulose in the suspension is generally present in an amount of 1-10 wt %, preferably 1-5 wt %, and more preferably 2-5 wt %, based on the total mass of the solid pharmaceutical composition. In some embodiments, lactose in the suspension is generally present in an amount of 1-45 wt %, preferably 5-30 wt %, and more preferably 5-20 wt %, based on the total mass of the solid pharmaceutical composition. In a specific embodiment, the mass ratio of the monomethanesulfonate of the compound of formula I to lactose in the suspension is generally 1:1 to 1:10, preferably 1:1 to 1:5, and more preferably 1:1 to 1:2. In some embodiments, sodium dodecyl sulfate in the suspension is generally present in an amount of 0.5-5 wt %, preferably 0.5-2 wt %, and more preferably 0.5-1 wt %, based on the total mass of the solid pharmaceutical composition.

In some embodiments, the fluidization excipient comprises a diluent and a disintegrant. The diluent is selected from: microcrystalline cellulose, lactose, starch, mannitol, xylitol, a mixture of microcrystalline cellulose and lactose, a mixture of microcrystalline cellulose and starch, a mixture of microcrystalline cellulose and mannitol, and a mixture of microcrystalline cellulose and xylitol; and preferably, microcrystalline cellulose, a mixture of microcrystalline cellulose and lactose, and a mixture of microcrystalline cellulose and mannitol. In some embodiments, the disintegrant is selected from: croscarmellose sodium, sodium carboxymethyl starch, crospovidone, and low substituted hydroxypropyl cellulose; and preferably, croscarmellose sodium.

In some embodiments, when the diluent in the fluidization excipient is a mixture of microcrystalline cellulose and another diluent, the another diluent may or may not be of the same kind as that of the diluent in the suspension comprising the monomethanesulfonate of the compound of formula I; preferably, the diluents are of the same kind.

In some embodiments, the fluidization excipient comprises microcrystalline cellulose and croscarmellose sodium.

In some embodiments, the fluidization excipient comprises microcrystalline cellulose, mannitol and croscarmellose sodium. In a specific embodiment, the mass ratio of microcrystalline cellulose to mannitol in the fluidization excipient is 1:1 to 9:1, preferably 1:1 to 5:1, and more preferably 2:1 to 4:1.

In some embodiments, the additional excipient comprises a lubricant. The lubricant is selected from: magnesium stearate, glyceryl behenate, sodium lauryl sulfate, and sodium stearyl fumarate; and preferably, magnesium stearate.

In some embodiments, the solid pharmaceutical composition comprising the monomethanesulfonate of the compound of formula I disclosed herein may comprise: a mixture comprising monomethanesulfonate of the compound of formula I, hydroxypropyl methylcellulose, mannitol, and sodium dodecyl sulfate; a fluidization excipient comprising microcrystalline cellulose and croscarmellose sodium; and an additional excipient comprising magnesium stearate. In some embodiments, the solid pharmaceutical composition comprising the monomethanesulfonate of the compound of formula I is prepared by fluidized bed granulation.

In some embodiments, the solid pharmaceutical composition comprising the monomethanesulfonate of the compound of formula I disclosed herein may comprise: a mixture comprising monomethanesulfonate of the compound of formula I, hydroxypropyl methylcellulose, mannitol, and sodium dodecyl sulfate; a fluidization excipient comprising microcrystalline cellulose, mannitol and croscarmellose sodium; and an additional excipient comprising magnesium stearate. In some embodiments, the solid pharmaceutical composition comprising the monomethanesulfonate of the compound of formula I is prepared by fluidized bed granulation.

In some embodiments, the solid pharmaceutical composition comprising the monomethanesulfonate of the compound of formula I disclosed herein may comprise: a mixture comprising monomethanesulfonate of the compound of formula I, hydroxypropyl cellulose, mannitol, and sodium dodecyl sulfate; a fluidization excipient comprising microcrystalline cellulose and croscarmellose sodium; and an additional excipient comprising magnesium stearate. In some embodiments, the solid pharmaceutical composition comprising the monomethanesulfonate of the compound of formula I is prepared by fluidized bed granulation.

In some embodiments, the solid pharmaceutical composition comprising the monomethanesulfonate of the compound of formula I disclosed herein may comprise: a mixture comprising monomethanesulfonate of the compound of formula I, hydroxypropyl cellulose, mannitol, and sodium dodecyl sulfate; a fluidization excipient comprising microcrystalline cellulose, mannitol and croscarmellose sodium; and an additional excipient comprising magnesium stearate. In some embodiments, the solid pharmaceutical composition comprising the monomethanesulfonate of the compound of formula I is prepared by fluidized bed granulation.

In some embodiments, the method for preparing the solid pharmaceutical composition comprising the monomethanesulfonate of the compound of formula I further comprises tableting; preferably, the method further comprises coating.

In the present application, the total mass of the solid pharmaceutical composition is on a dry basis, which does not include the solvents used in the preparation.

In the present application, sizing refers to the arrangement and classification of the dried granules for dispersing the agglomerated and adhered granules so as to give uniform granules with a certain particle size range. One of the common methods for sizing is sieving.

The solid pharmaceutical compositions of the monomethanesulfonate of the compound of formula I disclosed herein have the following advantages: when the suspension comprising the active ingredient comprises a diluent, the components of the solid pharmaceutical composition comprising the monomethanesulfonate of the compound of formula I, by fluidized bed granulation, can solve the problem of poor dissolution rate due to the insolubility of the monomethanesulfonate of the compound of formula I. Especially, when the diluent is mannitol, the dissolution rate is significantly improved. When the suspension comprises both diluent and solubilizer, the dissolution rate is improved to a most significant extent.

DETAILED DESCRIPTION

The following specific examples are intended to allow those skilled in the art to clearly understand and implement the present application. They should not be construed as limiting the scope of the present application, but as exemplary and representative illustrations of the present application.

Example 1

The monomethanesulfonate of the compound of formula I, microcrystalline cellulose, mannitol, hydroxypropyl methylcellulose, croscarmellose sodium and sodium dodecyl sulfate were sieved and mixed. The mixture was subjected to dry granulation and sizing, added with magnesium stearate and mixed well. Tablets were formed by dry tableting using a tableting machine. The feeding amount of materials was for 200 tablets, each tablet containing 50 mg of the compound of formula I. The formulation is shown in Table 1 below:

TABLE 1

| Components | Content, mg/tablet | Content, wt % |
|---|---|---|
| Monomethanesulfonate of compound of formula I | 60 | 20 |
| Microcrystalline cellulose | 132 | 44 |
| Mannitol | 72 | 24 |
| Hydroxypropyl methylcellulose | 6 | 2 |
| Croscarmellose sodium | 24 | 8 |
| Sodium dodecyl sulfate | 3 | 1 |
| Magnesium stearate | 3 | 1 |
| In total | 300 | 100 |

Example 2

Hydroxypropyl methylcellulose, mannitol and sodium dodecyl sulfate were dissolved in 540 mg of water. The monomethanesulfonate of the compound of formula I was added, and the mixture was sheared for dispersing to prepare a suspension. Microcrystalline cellulose and croscarmellose sodium were sieved and mixed to give a fluidization excipient for use. The suspension was sprayed to the fluidization excipient in a fluidized bed reactor, and the resulting fluid was subjected to granulating, in which the air input was controlled at 600 m$^3$/h, air input temperature at 70° C., and atomization pressure at 2.5 bar. The granules were dried with the temperature controlled at 75° C. or less and the water content ≤2.0%. The granules were sieved for sizing. Magnesium stearate was added before mixing well and tableting. The feeding amount of materials was for 200 tablets, each tablet containing 50 mg of the compound of formula I. The formulation is shown in Table 2 below:

TABLE 2

| Procedure | Components | Content, mg/tablet | Content, wt % |
|---|---|---|---|
| Suspension preparation | Monomethanesulfonate of compound of formula I | 60 | 19.8 |
| | Hydroxypropyl methylcellulose | 6 | 2 |
| | Mannitol | 72 | 23.8 |
| | Sodium dodecyl sulfate | 3 | 1 |
| Fluidization excipient | Microcrystalline cellulose | 135 | 44.5 |
| | Croscarmellose sodium | 24 | 7.9 |
| Additional excipient | Magnesium stearate | 3 | 1 |
| In total | | 303 | 100 |

Example 3

Mannitol and hydroxypropyl methylcellulose were dissolved in 540 mg of water. The monomethanesulfonate of the compound of formula I was added, and the mixture was sheared for dispersing to prepare a suspension. Microcrystalline cellulose and croscarmellose sodium were sieved and mixed to give a fluidization excipient for use. The suspension was sprayed to the fluidization excipient in a fluidized bed reactor, and the resulting fluid was subjected to granulating, in which the air input was controlled at 650 m$^3$/h, air input temperature at 65° C., and atomization pressure at 2.0 bar. The granules were dried with the temperature controlled at 75° C. or less and the water content ≤2.0%. The granules were sieved for sizing. Magnesium stearate was added before mixing well and tableting. The feeding amount of materials was for 200 tablets, each tablet containing 50 mg of the compound of formula I. The formulation is shown in Table 3 below:

TABLE 3

| Procedure | Components | Example 3 | Content, wt % |
|---|---|---|---|
| Suspension preparation | Monomethanesulfonate of compound of formula I | 60 | 20 |
| | Hydroxypropyl methylcellulose | 6 | 2 |
| | Mannitol | 72 | 24 |
| Fluidization excipient | Microcrystalline cellulose | 135 | 45 |
| | Croscarmellose sodium | 24 | 8 |
| Additional excipient | Magnesium stearate | 3 | 1 |
| In total | | 300 | 100 |

Example 4

Hydroxypropyl methylcellulose and sodium dodecyl sulfate were dissolved in 540 mg of water. The monomethanesulfonate of the compound of formula I was added, and the mixture was sheared for dispersing to prepare a suspension. Microcrystalline cellulose and croscarmellose sodium were sieved and mixed to give a fluidization excipient for use. The suspension was sprayed to the fluidization excipient in a fluidized bed reactor, and the resulting fluid was subjected to granulating, in which the air input was controlled at 600 m$^3$/h, air input temperature at 68° C., and atomization pressure at 2.0 bar. The granules were dried with the temperature controlled at 75° C. or less and the water content ≤2.0%. The granules were sieved for sizing. Magnesium stearate was added before mixing well and tableting. The feeding amount of materials was for 200 tablets, each tablet containing 50 mg of the compound of formula I. The formulation is shown in Table 4 below:

TABLE 4

| Procedure | Components | Example 4 | Content, wt % |
|---|---|---|---|
| Suspension preparation | Monomethanesulfonate of compound of formula I | 60 | 19.8 |
| | Hydroxypropyl methylcellulose | 6 | 2 |
| | Sodium dodecyl sulfate | 3 | 1 |

TABLE 4-continued

| Procedure | Components | Example 4 | Content, wt % |
|---|---|---|---|
| Fluidization excipient | Microcrystalline cellulose | 207 | 68.3 |
| | Croscarmellose sodium | 24 | 7.9 |
| Additional excipient | Magnesium stearate | 3 | 1 |
| In total | | 303 | 100 |

Example 5

Hydroxypropyl methylcellulose and sodium dodecyl sulfate were dissolved in 540 mg of water. The monomethanesulfonate of the compound of formula I was added, and the mixture was sheared for dispersing to prepare a suspension. Microcrystalline cellulose, mannitol and croscarmellose sodium were sieved and mixed to give a fluidization excipient for use. The suspension was sprayed to the fluidization excipient in a fluidized bed reactor, and the resulting fluid was subjected to granulating, in which the air input was controlled at 700 m$^3$/h, air input temperature at 65° C., and atomization pressure at 2.5 bar. The granules were dried with the temperature controlled at 75° C. or less and the water content≤2.0%. The granules were sieved for sizing. Magnesium stearate was added before mixing well and tableting. The feeding amount of materials was for 200 tablets, each tablet containing 50 mg of the compound of formula I. The formulation is shown in Table 5 below:

TABLE 5

| Procedure | Components | Example 5 | Content, wt % |
|---|---|---|---|
| Suspension preparation | Monomethanesulfonate of compound of formula I | 60 | 19.8 |
| | Hydroxypropyl methylcellulose | 6 | 2 |
| | Sodium dodecyl sulfate | 3 | 1 |
| Fluidization excipient | Microcrystalline cellulose | 135 | 44.5 |
| | Mannitol | 72 | 23.8 |
| | Croscarmellose sodium | 24 | 7.9 |
| Additional excipient | Magnesium stearate | 3 | 1 |
| In total | | 303 | 100 |

Example 6

Hydroxypropyl methylcellulose, mannitol and sodium dodecyl sulfate were dissolved in 540 mg of water. The monomethanesulfonate of the compound of formula I was added, and the mixture was sheared for dispersing to prepare a suspension. Microcrystalline cellulose, mannitol and croscarmellose sodium were sieved and mixed to give a fluidization excipient for use. The suspension was sprayed to the fluidization excipient in a fluidized bed reactor, and the resulting fluid was subjected to granulating, in which the air input was controlled at 700 m$^3$/h, air input temperature at 75° C., and atomization pressure at 2.5 bar. The granules were dried with the temperature controlled at 75° C. or less and the water content≤2.0%. The granules were sieved for sizing. Magnesium stearate was added before mixing well and tableting. The feeding amount of materials was for 200 tablets, each tablet containing 50 mg of the compound of formula I. The formulation is shown in Table 6 below:

TABLE 6

| Procedure | Components | Example 6 | Content, wt % |
|---|---|---|---|
| Suspension preparation | Monomethanesulfonate of compound of formula I | 60 | 19.8 |
| | Hydroxypropyl methylcellulose | 6 | 2 |
| | Mannitol | 36 | 11.9 |
| | Sodium dodecyl sulfate | 3 | 1 |
| Fluidization excipient | Microcrystalline cellulose | 135 | 44.5 |
| | Mannitol | 36 | 11.9 |
| | Croscarmellose sodium | 24 | 7.9 |
| Additional excipient | Magnesium stearate | 3 | 1 |
| In total | | 303 | 100 |

Example 7

Hydroxypropyl methylcellulose, mannitol and sodium dodecyl sulfate were dissolved in 540 mg of water. The monomethanesulfonate of the compound of formula I was added, and the mixture was sheared for dispersing to prepare a suspension. Microcrystalline cellulose and croscarmellose sodium were sieved and mixed to give a fluidization excipient for use. The suspension was sprayed to the fluidization excipient in a fluidized bed reactor, and the resulting fluid was subjected to granulating, in which the air input was controlled at 800 m$^3$/h, air input temperature at 75° C., and atomization pressure at 1.5 bar. The granules were dried with the temperature controlled at 75° C. or less and the water content≤2.0%. The granules were sieved for sizing. Magnesium stearate was added before mixing well and tableting. The feeding amount of materials was for 200 tablets, each tablet containing 50 mg of the compound of formula I. The formulation is shown in Table 7 below:

TABLE 7

| Procedure | Components | Example 7 | Content, wt % |
|---|---|---|---|
| Suspension preparation | Monomethanesulfonate of compound of formula I | 60 | 19.6 |
| | Hydroxypropyl methylcellulose | 6 | 2 |
| | Mannitol | 60 | 19.6 |
| | Sodium dodecyl sulfate | 3 | 1 |
| Fluidization excipient | Microcrystalline cellulose | 150 | 49 |
| | Croscarmellose sodium | 24 | 7.8 |
| Additional excipient | Magnesium stearate | 3 | 1 |
| In total | | 306 | 100 |

Example 8

Hydroxypropyl methylcellulose, lactose and sodium dodecyl sulfate were dissolved in 540 mg of water. The monomethanesulfonate of the compound of formula I was added, and the mixture was sheared for dispersing to prepare a suspension. Microcrystalline cellulose and croscarmellose sodium were sieved and mixed to give a fluidization excipient for use. The suspension was sprayed to the fluidization excipient in a fluidized bed reactor, and the resulting fluid was subjected to granulating, in which the air input was controlled at 700 m$^3$/h, air input temperature at 70° C., and atomization pressure at 1.5 bar. The granules were dried with the temperature controlled at 75° C. or less and the water content≤2.0%. The granules were sieved for sizing. Magnesium stearate was added before mixing well and tableting. The feeding amount of materials was for 200 tablets, each tablet containing 50 mg of the compound of formula I. The formulation is shown in Table 8 below:

TABLE 8

| Procedure | Components | Example 8 | Content, wt % |
|---|---|---|---|
| Suspension preparation | Monomethanesulfonate of compound of formula I | 60 | 19.8 |
|  | Hydroxypropyl methylcellulose | 6 | 2 |
|  | Lactose | 72 | 23.8 |
|  | Sodium dodecyl sulfate | 3 | 1 |
| Fluidization excipient | Microcrystalline cellulose | 135 | 44.5 |
|  | Croscarmellose sodium | 24 | 7.9 |
| Additional excipient | Magnesium stearate | 3 | 1 |
| In total |  | 303 | 100 |

Example 9

Hydroxypropyl cellulose, sodium dodecyl sulfate and mannitol were dissolved in 540 mg of water. The monomethanesulfonate of the compound of formula I was added, and the mixture was sheared for dispersing to prepare a suspension. Microcrystalline cellulose and croscarmellose sodium were sieved and mixed to give a fluidization excipient for use. The suspension was sprayed to the fluidization excipient in a fluidized bed reactor, and the resulting fluid was subjected to granulating, in which the air input was controlled at 750 m$^3$/h, air input temperature at 75° C., and atomization pressure at 2.5 bar. The granules were dried with the temperature controlled at 75° C. or less and the water content≤2.0%. The granules were sieved for sizing. Magnesium stearate was added before mixing well and tableting. The feeding amount of materials was for 200 tablets, each tablet containing 50 mg of the compound of formula I. The formulation is shown in Table 9 below:

TABLE 9

| Procedure | Components | Example 9 | Content, wt % |
|---|---|---|---|
| Suspension preparation | Monomethanesulfonate of compound of formula I | 60 | 19.8 |
|  | Hydroxypropyl cellulose | 6 | 2 |
|  | Mannitol | 72 | 23.8 |
|  | Sodium dodecyl sulfate | 3 | 1 |

TABLE 9-continued

| Procedure | Components | Example 9 | Content, wt % |
|---|---|---|---|
| Fluidization excipient | Microcrystalline cellulose | 135 | 44.5 |
|  | Croscarmellose sodium | 24 | 7.9 |
| Additional excipient | Magnesium stearate | 3 | 1 |
| In total |  | 303 | 303 |

Experimental Example 1: Comparison of Stability

The tablets of Examples 1 and 2 were stored at 40° C. and 75% relative humidity for 3 months before the total impurities and dissolution rate were measured. Dissolution rate was measured according to the Method 2 (paddle, 0.1 M hydrochloric acid medium, 1000 mL, 75 rpm) of General Chapter 0931, Chinese Pharmacopoeia, Volume IV, 2015 Edition. The stability results are shown in Table 10.

TABLE 10

Stability results of Examples 1 and 2

|  | Example 1 | | Example 2 | |
|---|---|---|---|---|
| Time | Total impurities | Dissolution rate | Total impurities | Dissolution rate |
| Month 0 | 0.15% | 50 | 0.19% | 86 |
| Month 1 | 0.25% | 30 | 0.23% | 80 |
| Month 2 | 0.30% | 31 | 0.25% | 81 |
| Month 3 | 0.45% | 30 | 0.27% | 80 |

The results in Table 10 show that: for the tablets of Example 1, the total impurities increased and the dissolution rate decreased significantly over time; whereas the tablets of example 2 substantially showed no increase in total impurities and no decrease in dissolution rate over time.

Experimental Example 2: Comparison of Dissolution Rate

Figure 1:
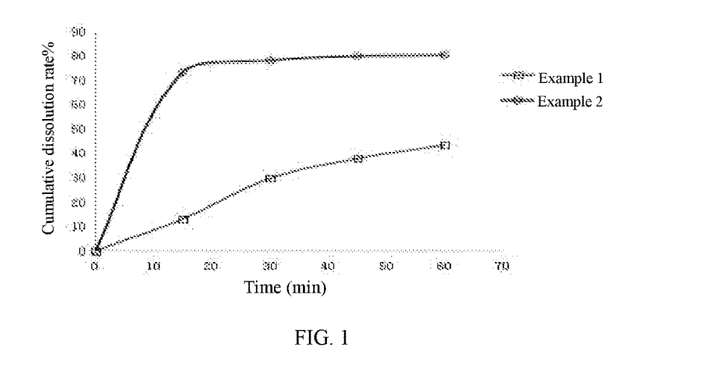
FIG. 1 illustrates the comparison of dissolution profiles of tablets according to Examples 1 and 2.
Figure 2:
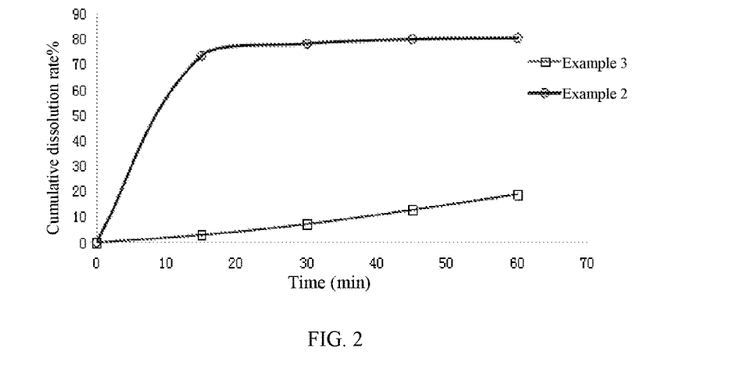
FIG. 2 illustrates the comparison of dissolution profiles of tablets according to Examples 2 and 3.
Figure 3:
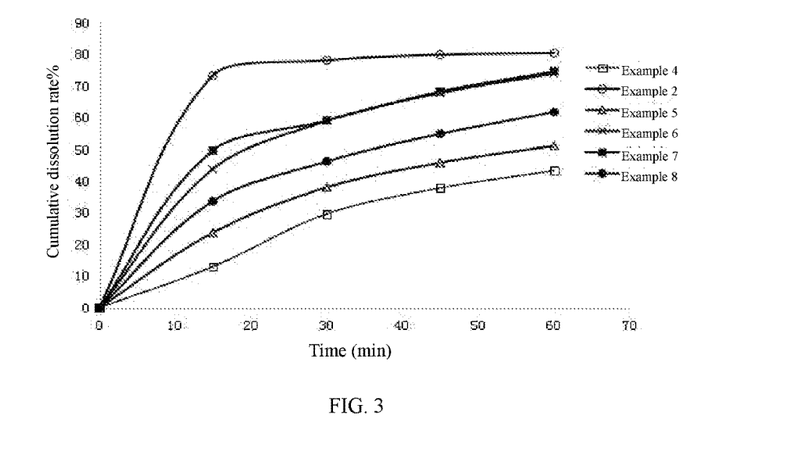
FIG. 3 illustrates the comparison of dissolution profiles of tablets according to Examples 2, 4, 5, 6, 7 and 8.
Figure 4:
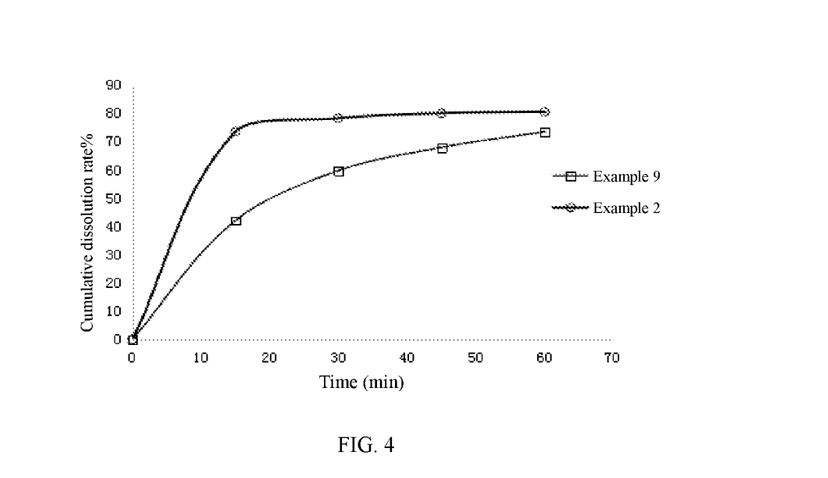
FIG. 4 illustrates the comparison of dissolution profiles of tablets according to Examples 2 and 9.

The dissolution profiles for tablets from Examples 1-9 were measured according to the Method 2 (paddle, 0.1 M hydrochloric acid medium, 1000 mL, 75 rpm) of General Chapter 0931, Chinese Pharmacopoeia, Volume IV, 2015 Edition. The comparison of dissolution profiles of Examples 1 and 2 is shown in FIG. 1; the comparison of Examples 2 and 3 is shown in FIG. 2; the comparison of Examples 2, 4, 5, 6, 7 and 8 is shown in FIG. 3. The comparison of Examples 2 and 9 is shown in FIG. 4.

Experimental Example 3: Comparison of In Vivo Bioavailability

Figure 5:
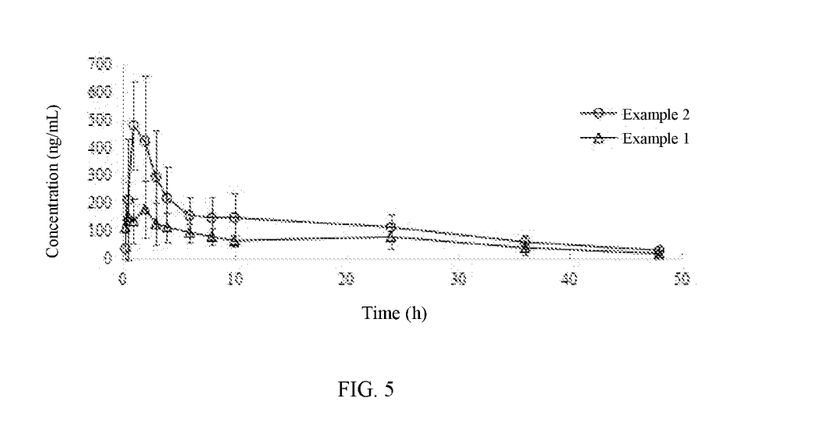
FIG. 5 illustrates the comparison of the in vivo bioavailability of tablets according to Examples 1 and 2.

The tablets of Examples 1 and 2 were subjected to a bioavailability test in beagle dogs by oral administration (specification: 50 mg, 1 tablet/dog). The test results are shown in FIG. 5, suggesting that the in vivo bioavailability of the tablets prepared in Example 2 is significantly higher than that of Example 1.

The invention claimed is:

1. A solid pharmaceutical composition, comprising a mixture comprising monomethanesulfonate of the compound of formula I, and a fluidization excipient, wherein the mixture comprising the monomethanesulfonate of the compound of formula I further comprises a binder, a solubilizer and a diluent;

Formula I wherein the solid pharmaceutical composition comprises 10-100 mg of the monomethanesulfonate of the compound of formula I; or alternatively, the monomethanesulfonate of the compound of formula I is present in an amount of 0.5-50 wt %, based on the total mass of the solid pharmaceutical composition;

wherein the binder is selected from hydroxypropyl methylcellulose, hydroxypropyl cellulose and povidone; the solubilizer is selected from sodium dodecyl sulfate and magnesium dodecyl sulfate; and the diluent is mannitol.

2. The solid pharmaceutical composition according to claim 1, wherein a binder is present in an amount of 1-10 wt %, based on the solid pharmaceutical composition; or, the solubilizer is present in an amount of 0.5-5 wt % based on the solid pharmaceutical composition; or a diluent in the solid pharmaceutical composition is present in an amount of 10-90 wt %, based on the solid pharmaceutical composition.

3. The solid pharmaceutical composition according to claim 1 further comprising an additional excipient.

4. The solid pharmaceutical composition according to claim 1, wherein the diluent in the mixture comprising the monomethanesulfonate of the compound of formula I is present in an amount of 10-50 wt %, based on the total amount of diluents in the solid pharmaceutical composition; or, the diluent in the mixture comprising the monomethanesulfonate of the compound of formula I is present in an amount of 1-45 wt %, based on the total mass of the solid pharmaceutical composition; or, the mass ratio of the monomethanesulfonate of the compound of formula I to the diluent in the mixture is 1:0.5 to 1:10.

5. The solid pharmaceutical composition according to claim 1, wherein the fluidization excipient comprises a diluent and a disintegrant.

6. The solid pharmaceutical composition according to claim 3, wherein the additional excipient comprises a lubricant.

7. The solid pharmaceutical composition according to claim 1, wherein the solid pharmaceutical composition is prepared by fluidized bed granulation.

8. A method for preparing the solid pharmaceutical composition according to claim 1, wherein the method is fluidized bed granulation, comprising: (1) preparing a suspension comprising the monomethanesulfonate of the compound of formula I, the suspension further comprises a binder selected from hydroxypropyl methylcellulose, hydroxypropyl cellulose and povidone, a solubilizer selected from sodium dodecyl sulfate and magnesium dodecyl sulfate, and a diluent is mannitol; (2) preparing a fluidization excipient; (3) placing the fluidization excipient into a fluidized bed, and spraying the suspension comprising the monomethanesulfonate of the compound of formula I into the fluidized bed for granulation; (4) sizing; and optionally (5) mixing an additional excipient with the sized materials.

9. The method according to claim 8, wherein, in step (1), a solvent of the suspension is selected from methanol, ethanol, isopropanol, acetone, water, and any combination thereof; and the mass ratio of the monomethanesulfonate of the compound of formula I to the solvent in the suspension is 1:(5-20).

10. The method according to claim 8, wherein in step (1), the monomethanesulfonate of the compound of formula I is first mixed with the binder, the diluent and/or the solubilizer to give a mixture comprising the monomethanesulfonate of the compound of formula I, and then the mixture is mixed with the solvent to give the suspension comprising the monomethanesulfonate of the compound of formula I; or, after step (3), the granulation process in the fluidized bed further comprises drying to remove the solvent from the suspension.

11. The solid pharmaceutical composition according to claim 1, wherein the binder in the mixture comprising the monomethanesulfonate of the compound of formula I is selected from hydroxypropyl methylcellulose and hydroxypropyl cellulose.

12. The solid pharmaceutical composition according to claim 2, wherein the solubilizer in the mixture comprising the monomethanesulfonate of the compound of formula I is sodium dodecyl sulfate.

13. The solid pharmaceutical composition according to claim 5, wherein the diluent in the fluidization excipient is selected from microcrystalline cellulose, lactose, starch, mannitol, xylitol, a mixture of microcrystalline cellulose and lactose, a mixture of microcrystalline cellulose and starch, a mixture of microcrystalline cellulose and mannitol, and a mixture of microcrystalline cellulose and xylitol; and the disintegrant in the fluidization excipient is selected from croscarmellose sodium, sodium carboxymethyl starch, crospovidone and low substituted hydroxypropyl cellulose, and the disintegrant is present in an amount of 1-10 wt %, based on the solid pharmaceutical composition.

14. The solid pharmaceutical composition according to claim 6, wherein the lubricant is selected from magnesium stearate, glyceryl behenate, sodium lauryl sulfate, and sodium stearyl fumarate, and the lubricant is present in an amount of 0.5-5 wt %, based on the solid pharmaceutical composition.

15. The solid pharmaceutical composition according to claim 1, wherein the solid pharmaceutical composition is a tablet, pill, capsule, powder, or granule.

16. The method according claim 8, comprising (1) preparing the suspension comprising the monomethanesulfonate of the compound of formula I, the binder, the solubilizer and the diluent; (2) mixing a diluent with a disintegrant to give the fluidization excipient; (3) placing the fluidization excipient of step (2) into a fluidized bed reactor, and spraying the suspension of step (1) into the fluidized bed for granulation; (4) sizing; and optionally (5) mixing a lubricant with a sized material from step (4).

17. The method according claim 16, wherein, in step (3), an air input in the fluidized bed reactor is 200-1000 m³/h; an air input temperature in the fluidized bed reactor is 40-80° C.; and the suspension is sprayed into the fluidized bed at an atomization pressure of 1-5 bar.

* * * * *